(12) United States Patent
Rabiner et al.

(10) Patent No.: US 6,695,781 B2
(45) Date of Patent: *Feb. 24, 2004

(54) ULTRASONIC MEDICAL DEVICE FOR TISSUE REMODELING

(75) Inventors: Robert A. Rabiner, North Reading, MA (US); Bradley A. Hare, Chelmsford, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 100 days.

This patent is subject to a terminal disclaimer.

(21) Appl. No.: 09/917,471

(22) Filed: Jul. 27, 2001

(65) Prior Publication Data

US 2002/0029054 A1 Mar. 7, 2002

Related U.S. Application Data

(63) Continuation-in-part of application No. 09/625,803, filed on Jul. 26, 2000.
(60) Provisional application No. 60/157,824, filed on Oct. 5, 1999, and provisional application No. 60/225,060, filed on Aug. 14, 2000.

(51) Int. Cl.[7] .................................................. A61N 7/00
(52) U.S. Cl. ............................ 600/439; 601/4; 604/22
(58) Field of Search ................................. 600/104, 121, 600/122, 123, 135, 139, 140, 141, 153, 154, 155, 156, 160–165, 439, 437; 601/2–4; 606/169, 46, 171, 180; 604/22

(56) References Cited

U.S. PATENT DOCUMENTS

| | | | |
|---|---|---|---|
| 3,805,787 A | 4/1974 | Banko | 128/276 |
| 4,474,180 A | 10/1984 | Angulo | 128/328 |
| 4,504,264 A | 3/1985 | Kelman | 604/22 |
| 4,750,488 A | 6/1988 | Wuchinich et al. | 128/303 |
| 4,886,491 A | 12/1989 | Parisi et al. | 604/22 |
| 4,920,954 A | 5/1990 | Alliger et al. | 128/24 |
| 4,922,902 A | 5/1990 | Wuchinich et al. | 604/22 |
| 4,931,047 A | 6/1990 | Broadwin et al. | 604/22 |
| 4,961,424 A | 10/1990 | Kubota et al. | 128/24 |
| 4,989,583 A | 2/1991 | Hood | 128/24 |
| 5,015,221 A | 5/1991 | Smith | 475/19 |
| 5,112,300 A | 5/1992 | Ureche | 604/22 |
| 5,163,421 A | 11/1992 | Bernstein et al. | 128/24.1 |
| 5,180,363 A | 1/1993 | Idemoto et al. | 202/32 |
| 5,255,669 A * | 10/1993 | Kubota et al. | 601/3 |
| 5,269,297 A | 12/1993 | Weng et al. | 128/24 |
| 5,380,274 A | 1/1995 | Nita | 604/22 |
| 5,419,761 A | 5/1995 | Narayanan et al. | 604/22 |
| 5,469,853 A | 11/1995 | Law et al. | 128/662.06 |
| 5,507,738 A * | 4/1996 | Ciervo | 606/1 |
| 5,527,273 A | 6/1996 | Manna et al. | 604/22 |
| 5,676,649 A | 10/1997 | Boukhny et al. | 604/22 |
| 5,725,494 A | 3/1998 | Brisken | 604/22 |
| 5,728,062 A | 3/1998 | Brisken | 604/22 |
| 5,735,811 A | 4/1998 | Brisken | 604/22 |
| 5,813,998 A * | 9/1998 | Dias | 601/2 |
| 5,931,805 A | 8/1999 | Brisken | 604/22 |
| 5,989,208 A | 11/1999 | Nita | 604/22 |
| 6,033,375 A | 3/2000 | Brumbach | 604/22 |
| 6,224,565 B1 | 5/2001 | Cimino | 604/22 |
| 6,524,251 B2 * | 2/2003 | Rabiner et al. | 600/439 |
| 2002/0077550 A1 * | 6/2002 | Rabiner et al. | 600/439 |
| 2002/0077643 A1 * | 6/2002 | Rabiner et al. | 606/169 |
| 2002/0107446 A1 * | 8/2002 | Rabiner et al. | 600/439 |

FOREIGN PATENT DOCUMENTS

| | | | |
|---|---|---|---|
| EP | 0493047 A1 | 1/1992 | F16H/7/12 |

\* cited by examiner

*Primary Examiner*—Eleni Mantis Mercader
(74) *Attorney, Agent, or Firm*—Palmer & Dodge, LLP; Richard B. Smith; David J. Dykeman

(57) ABSTRACT

A method for destructing, reducing or removing mammalian tissue with an ultrasonic device IS disclosed, comprising contacting the tissue with a transverse mode ultrasonic probe, and transmitting ultrasonic energy to the probe, until the tissue is fragmented by emulsification. The probe can be used with acoustic and/or aspirations sheaths to enhance destruction and removal of an occlusion and in combination with an imaging device to effect remodeling of human tissue in medical and cosmetic surgical procedures.

28 Claims, 11 Drawing Sheets

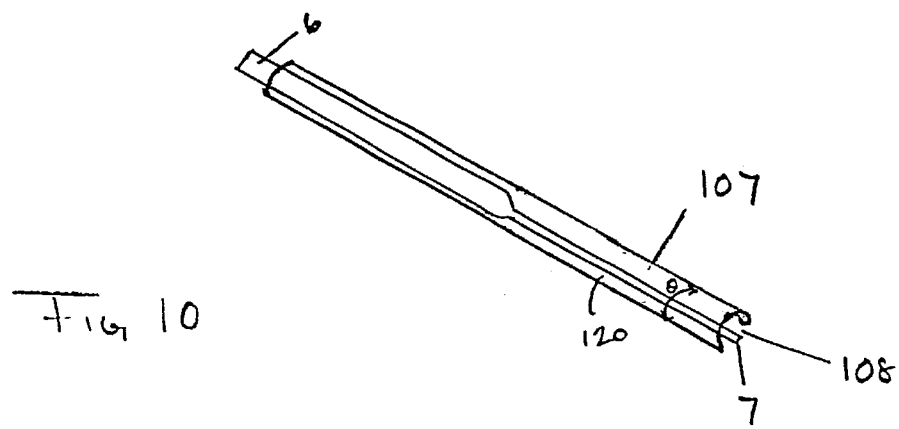
Fig 10
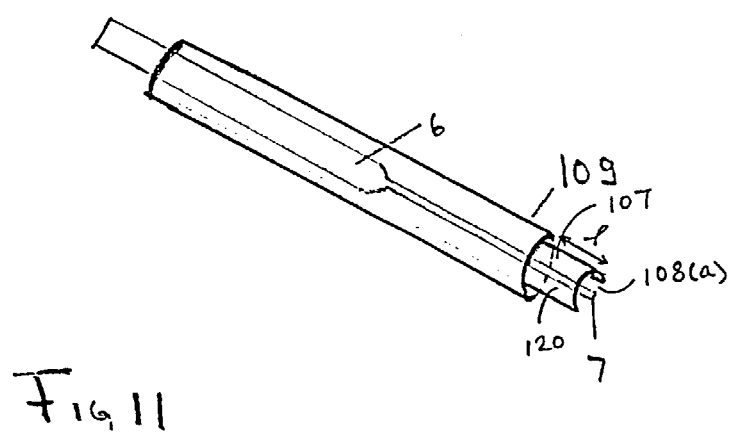
Fig 11
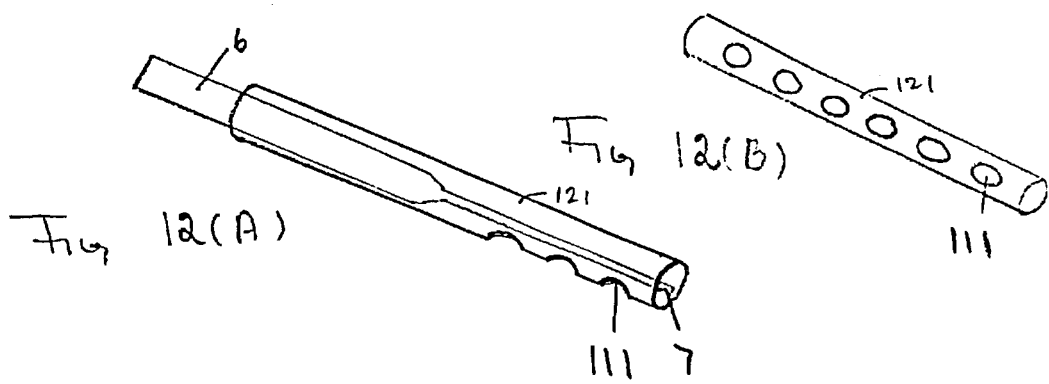
Fig 12(A)
Fig 12(B)

ULTRASONIC MEDICAL DEVICE FOR TISSUE REMODELING

RELATED APPLICATIONS

This application is a continuation in part of U.S. application Ser. No. 09/625,803 filed on Jul. 26, 2000 which claims priority to U.S. Provisional Application No. 60/157,824 filed on Oct. 5, 1999, and claims the benefit of U.S. Provisional Application No. 60/225,060 filed on Aug. 14, 2000, the entirety of which is incorporated herein by reference.

FIELD OF THE INVENTION

The present invention relates generally to medical devices, and more particularly to an ultrasonic medical device operating in a transverse mode for removal and remodeling of mammalian tissue in a controlled manner.

BACKGROUND OF THE INVENTION

Demands for sculpting and improving body shape and its function using plastic surgery have become widespread and are frequently reasoned by the patient's desire for such improvement. As a result, in addition to medically required surgical procedures for correcting congenital tissue malformations such as cleft palate, tissue remodeling is also performed for purely cosmetic reasons, e.g. to remove excessive fat tissue, correct hanging eye lids and to remove benign cysts, e.g. from the breast tissue. Generally, surgical methods involved in such procedures cause trauma, e.g., in the form of bruising and scarring, and patient discomfort. Furthermore, costs of postoperative treatment and recovery time can be substantial. Tissue removal using thermal methods, such as with laser devices, is often painful, and cause necrosis of the tissue area surrounding the surgical site that may require several weeks to heal. Therefore, surgical methods for tissue removal that are site specific in their mode of action and can be used with minimal trauma to tissue areas proximal to the surgical site are preferred, especially in the cosmetic procedures.

Medical devices utilizing ultrasonic energy to destroy tissue in the human body are known in the art. A major drawback of existing devices comprising an ultrasonic probe for tissue removal is that they are relatively slow in comparison procedures that involve surgical excision. This is mainly attributed to the fact that such ultrasonic devices rely on imparting ultrasonic energy to contacting tissue by undergoing a longitudinal vibration of the probe tip, wherein the probe tip is mechanically vibrated at an ultrasonic frequency a direction parallel to the probe longitudinal axis. This, in turn, produces a tissue destroying effect that is entirely localized at the probe tip, which substantially limits its ability to ablate large tissue areas in a short time.

One solution that has been proposed is to vibrate the tip of the probe in a transverse direction—i.e. perpendicular to the longitudinal axis of the probe—in addition to vibrating the tip in the longitudinal direction. For example, U.S. Pat. No. 4,961,424 to Kubota et al. discloses an ultrasonic treatment device to destroy and emulsify concretions or tissue in a human body. The Kubota et al. device produces both a longitudinal and transverse motion at the tip of the probe. The Kubota et al. patent, however, still relies solely on the tip of the probe to act as a working surface. Therefore, it improves the efficiency of the tip, but still relies on the tip of the probe to perform all cutting actions.

Although Kubota et al. describe providing a transverse motion at the tip of the probe, a transverse motion along the length of the probe has generally been discouraged. For example, U.S. Pat. No. 4,474,180 to Angulo discloses an ultrasonic kidney stone disintegration instrument with a damping material applied to the wire probe to inhibit lateral vibrations of the wire in the region of the connection to the ultrasonic transducer.

Another proposed method of improving the speed of ultrasonic tissue remove is oscillating the tip of the probe in addition to longitudinally vibrating the tip of the probe. For example, U.S. Pat. No. 4,504,264 to Kelman discloses an ultrasonic treatment device which improves the speed of ultrasonic tissue removal. In the Kelman device, the tip of the probe is vibrated longitudinally and also oscillated, so that the cutting efficiency of the probe tip is improved. Again, however, only the tip of the probe performs a cutting action.

SUMMARY OF THE INVENTION

The present invention is directed to a method and an apparatus for treating tissue using ultrasonic energy. The present invention has particular application in removal of adipose tissue in an individual. The invention is further applicable in removal of tissue in eyelids during corrective surgery. The method of the present invention can also be used to remove benign cysts in the breast tissue. The apparatus of the present invention is designed to have a small cross-sectional profile, therefore allowing the apparatus to be used in a minimally invasive manner. As a result, the present invention is advantageous in that it can be used in cosmetic surgical applications in both traditional surgical sites and out patient treatment with minimal postoperative complications and minimal damage to areas other than the area of treatment. The present invention therefore provides distinct advantages over the prior art in the cosmetic surgical procedures, and therefore provides an improved method of cosmetic surgical procedures.

BRIEF DESCRIPTION OF THE DRAWINGS

FIG. 10 shows a semi-cylindrical sheath having an aperture that is used to direct the transverse cavitation energy towards the tissue that is to be remodeled.

FIG. 11 shows a cylindrical sheath that can be used to cover the aperture of the semi-cylindrical sheath of FIG. 10 of the ultrasonic probe and further locally direct the cavitation energy.

FIG. 12 shows a cylindrical sheath that has multiple apertures for directing the cavitation energy locally. 12(A) is a side view of the sheath. 12(B) is a view of the sheath from below showing the side of the apertures.

DETAILED DESCRIPTION OF THE INVENTION

The present invention discloses a method for using a thin probe transmitting transverse ultrasonic energy along its length to remove adipose tissue or fat along the length of the probe. The invention further provides the use of said probe to remove benign cysts or cell growth in the breast tissue. The invention also provides the use of said probe to remove tissue from the eye lid, including the ocular sac. The ultrasonic tip of the present invention does not have to be sharp, because is uses cavitation, not the physical shape, as the mode of tissue removal. Therefore, the tip can be smooth making insertion less traumatic and less prone to residual tissue damage.

The ultrasonic energy to be applied to a particular treatment site is a function of the amplitude and frequency. In general, the throw rate or amplitude of the energy supplied by the apparatus of the present invention is in the range of 150 microns to 250 microns, and the frequency in the range of 20–80 kHz.

Figure 1:
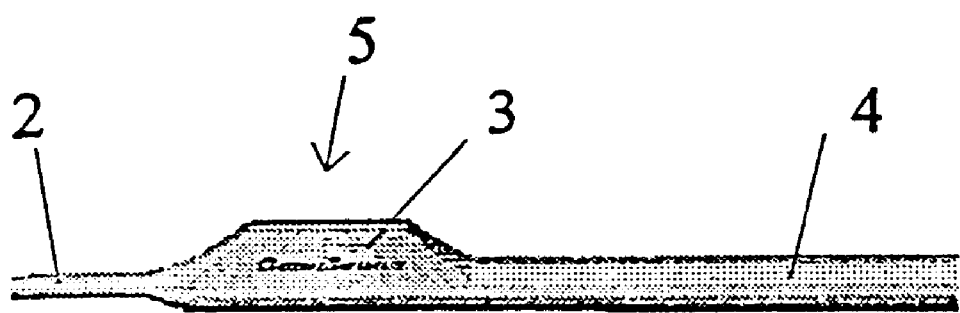
FIG. 1 is a side elevation view of handle of the ultrasonic treatment apparatus of the present invention.

FIG. 1 shows an embodiment of a handle 5 used with the present invention. The handle 5 is composed of an irrigation fitting or luer 2, a grasping area 3, and a probe fitting 4. The irrigation fitting or luer 2 is configured for connection with a flexible tube which is in turn connected to a source of pressurized irrigating fluid, such as water. The grasping area 3 is shaped for grasping by the hand of the apparatus operator, such as a surgeon, and may include one or more trigger or button mechanisms for activating and deactivating various features of the apparatus, such as suction, irrigation, power, etc.

Figure 2:
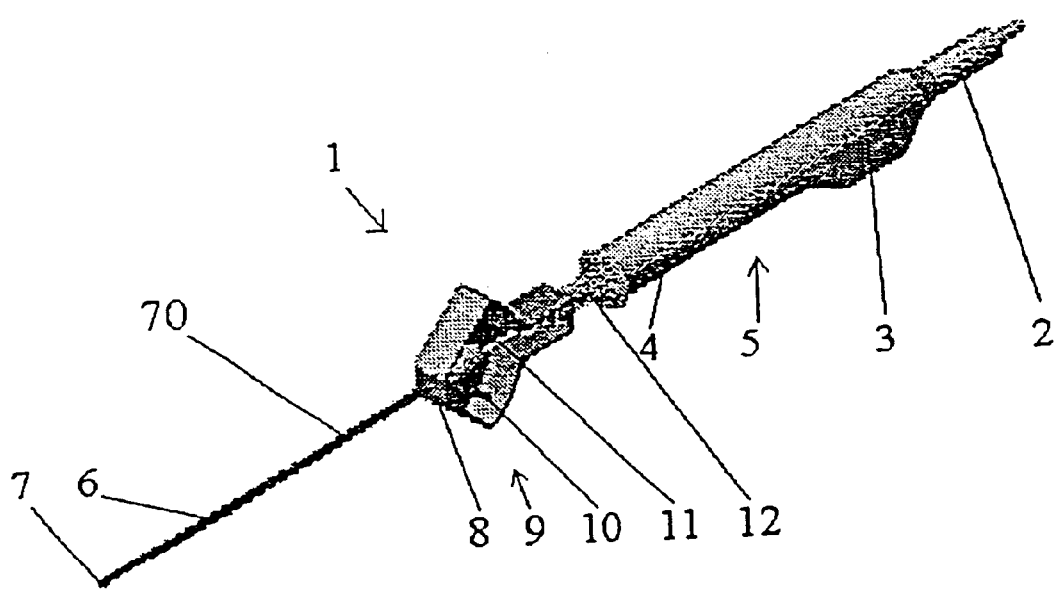
FIG. 2 is a perspective view of a first embodiment of the ultrasonic treatment apparatus of the present invention.
Figure 3:
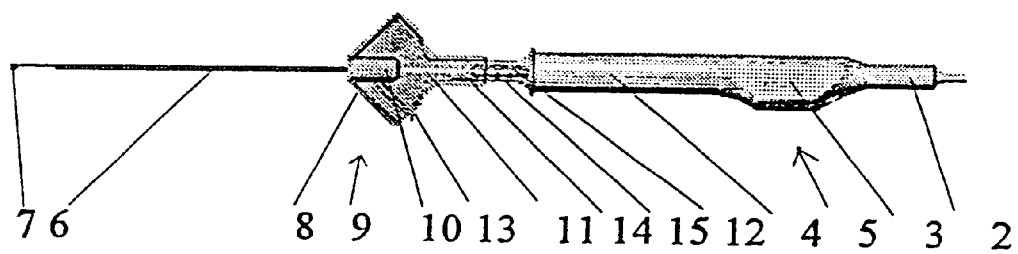
FIG. 3 is a side elevation view of the embodiment of FIG. 2.

FIGS. 2 and 3 show an embodiment of the ultrasonic treatment apparatus 1 of the present invention, which includes the handle 5 shown in FIG. 1. The ultrasonic treatment apparatus 1 includes an ultrasonic probe 6 with an ultrasonic probe tip 7. The ultrasonic probe 6 is axially movably mounted within an aspiration sheath or catheter 70, so that the probe tip 7 may move axially inwardly and outwardly relative to the distal end of the aspiration sheath or catheter 70. The ultrasonic probe 6 and aspiration sheath or catheter 70 are both mounted in an aspiration shroud 9, which includes an aspiration shroud housing 8. Within aspiration shroud housing 8 is an aspiration end 10 of aspiration sheath or catheter 70, which transmits suction or negative pressure to the interior of aspiration sheath or catheter 70. The aspiration end surrounds, and is sealed against, the ultrasonic transmission element 11 which extends to, and forms a proximal portion of, the ultrasonic probe 6. The aspiration end 10 is connected an aspiration fitting or luer 13. The aspiration fitting or luer 13 is configured for connection with a flexible tube which, in turn, is connected to a source of reduced pressure. The aspiration sheath is slidable relative to handle 5 and probe 6, thereby allowing the distance between the ultrasonic tip 7 and the distal end of the aspiration sheath or catheter 70 to be varied. An actuation mechanism 12 may extend from the aspiration shroud 9 to the handle 5, and is surrounded by suitable covers 14 and 15.

Figure 4:
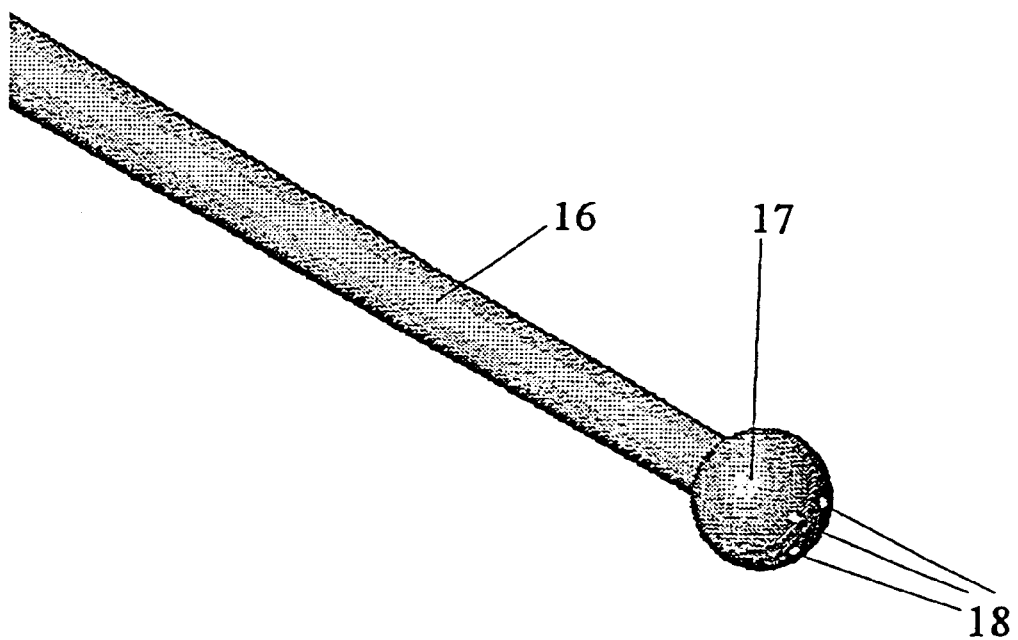
FIG. 4 is a perspective view of one embodiment of an ultrasonic tip of the present invention.

FIG. 4 shows an embodiment of an ultrasonic probe 16 and ultrasonic probe tip 17 of the present invention. The body of the ultrasonic probe 16 in the embodiment of FIG. 4 is preferably slightly tapered from the distal end to the proximal end. The ultrasonic tip 17 is in the form of a ball-shaped projection from the end of the ultrasonic probe 16. This shape of the ultrasonic tip 17 eliminates any sharp edges or surfaces on the tip which could result in damage to tissue during insertion, treatment or removal. The ultrasonic tip 17, at its distal surface, includes one or more irrigation ports 18. The irrigation ports 18 are all connected to an internal irrigation passage, preferably centrally located in the ultrasonic tip 17 and the ultrasonic probe 16. In addition to the configuration shown in FIG. 4, the ultrasonic probe 16 can have, extending along its length, one or more grooves or channels for aspiration, as discussed in more detail below.

Figure 5:
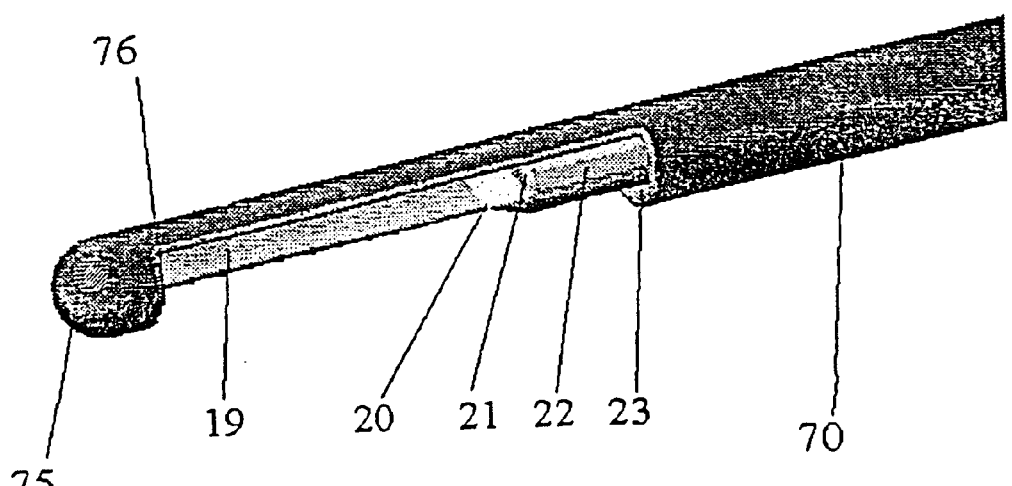
FIG. 5 is a perspective view of a second embodiment of an ultrasonic tip of the present invention.

FIG. 5 shows a second embodiment of the ultrasonic probe aspiration sheath or catheter of the present invention. In the embodiment of FIG. 5, the tip 75 of the aspiration sheath or catheter 70 is a rounded end. The aspiration sheath or catheter 70 includes a lateral slot or opening 19 on one side. The ultrasonic probe 23, with an ultrasonic probe tip 21 which may optionally include a bevel 20, is mounted for axial sliding movement within the aspiration sheath or catheter 70. At least one aspiration passage 23 is created in the space between the ultrasonic probe 22 and the interior wall of the aspiration sheath or catheter 70. Accordingly, as suction is applied to the aspiration fitting or luer 13, a negative pressure or suction is formed at the aspiration passage 23, to draw away and destroyed or cavitated tissue and any residual or irrigation fluid.

At the proximal end of the tip 75 is a grasping surface or backstop 76. This grasping surface or backstop 76 serves as an opposed surface to the ultrasonic tip 21, thereby allowing, e.g., dangle or loose treatment areas to be grasped during treatment. In operation, the aspiration sheath or catheter 70 is directed to a treatment area, until the dangling or loose treatment area falls into the lateral slot or opening 19. During this step, the ultrasonic probe 23 is in a retracted position, as shown in FIG. 5. Thereafter, the ultrasonic probe 23 is advanced axially outward, until the dangling or loose treatment area is clamped between the ultrasonic tip 21 and the grasping surface or backstop 76. Thereafter, the ultrasonic vibration generator is activated, such that ultrasonic energy is transmitted to the ultrasonic tip 21. As a result, the grasped treatment area is treated using ultrasonic energy and the resulting cavitation.

Figure 7:
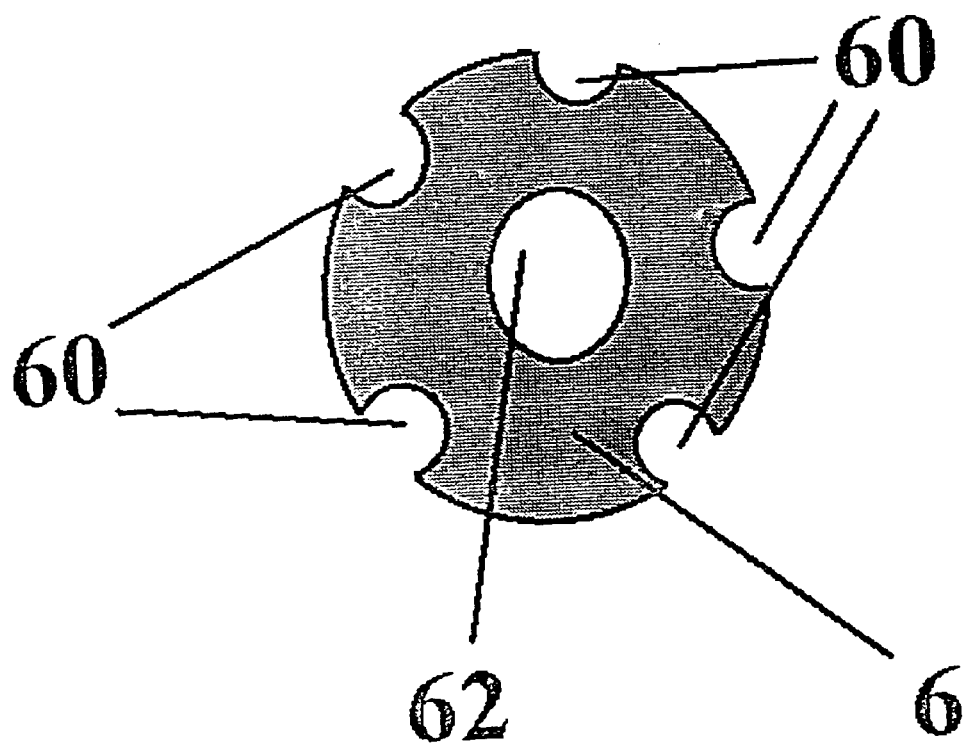
FIG. 7 is a radial cross-sectional view through an embodiment of an ultrasonic probe of the present invention.
Figure 9:
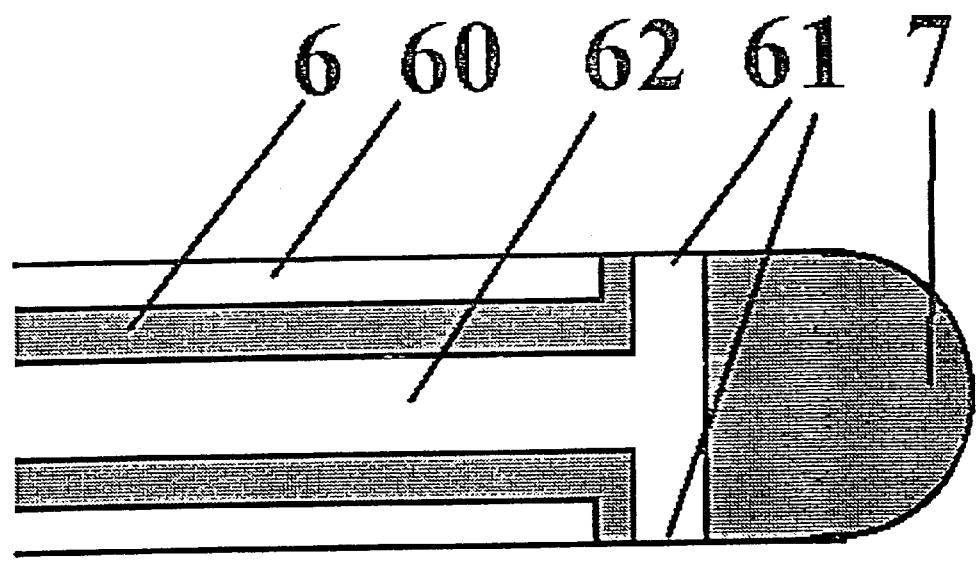
FIG. 9 is an axial cross-section of one embodiment of an ultrasonic treatment probe of the present invention.

FIGS. 7 and 9 show a radial cross-section through an ultrasonic probe 6 according to one embodiment of the invention. The probe 6 includes a central passage 62 which is connected to the irrigation fitting or luer 2. The central passage 62 terminates in two lateral lumens 61, located on the sides of the probe 6. The central passage 62 is used to transmit an irrigating fluid to the area around the ultrasonic tip 7, to thereby regulate the temperature of the treatment site. The irrigation fluid, together with the cavitational action of the ultrasonic tip 7, allows the treatment site to be regulated to a temperature of ±7° of normal body temperature. Furthermore, because the lumens 61 do not pass through the ultrasonic tip 7, the effective area of treatment of the ultrasonic tip 7 is increased.

As shown in FIGS. 7 and 9, the outer surface of the ultrasonic probe 6 includes one or more grooves or channels 60. These grooves or channels, although straight in FIG. 9, could spiral along the length of the ultrasonic probe 6. The grooves or channels 60 are used to aspirate fluid and tissue fragments from the treatment site, as the result of negative pressure or suction applied at the proximal ends of the grooves or channels 60. As a result, fluid and tissue fragments travel down the grooves or channels 60 and away from the treatment site, thereby preventing fluid and fragments from interfering with the ultrasonic processing and cavitation of additional tissue.

Figure 6:
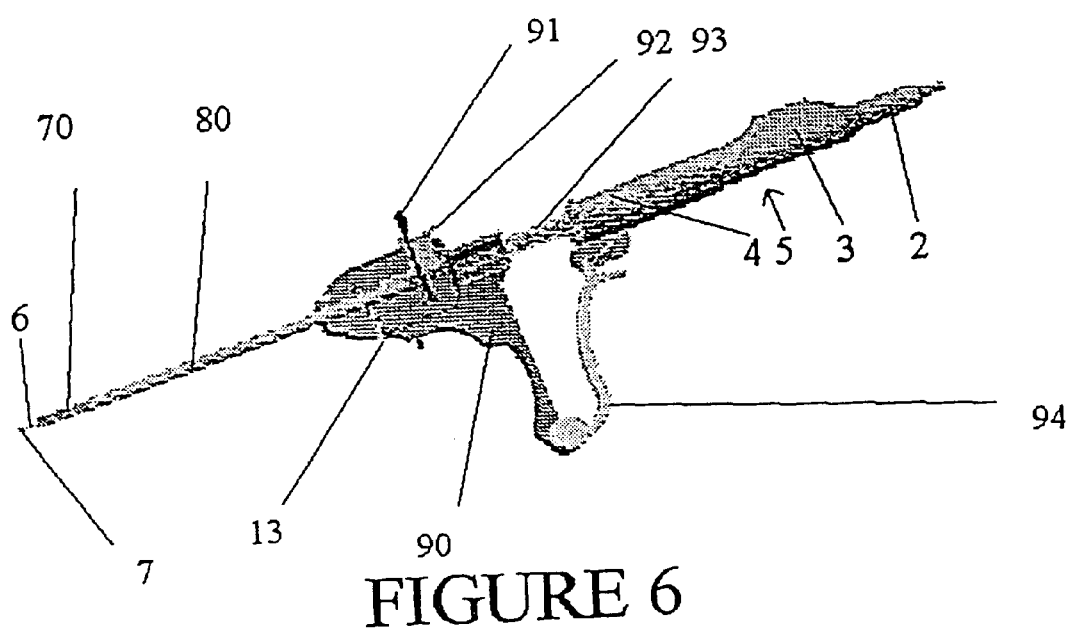
FIG. 6 is a side elevation view of a second embodiment of an ultrasonic treatment apparatus of the present invention.
Figure 8:
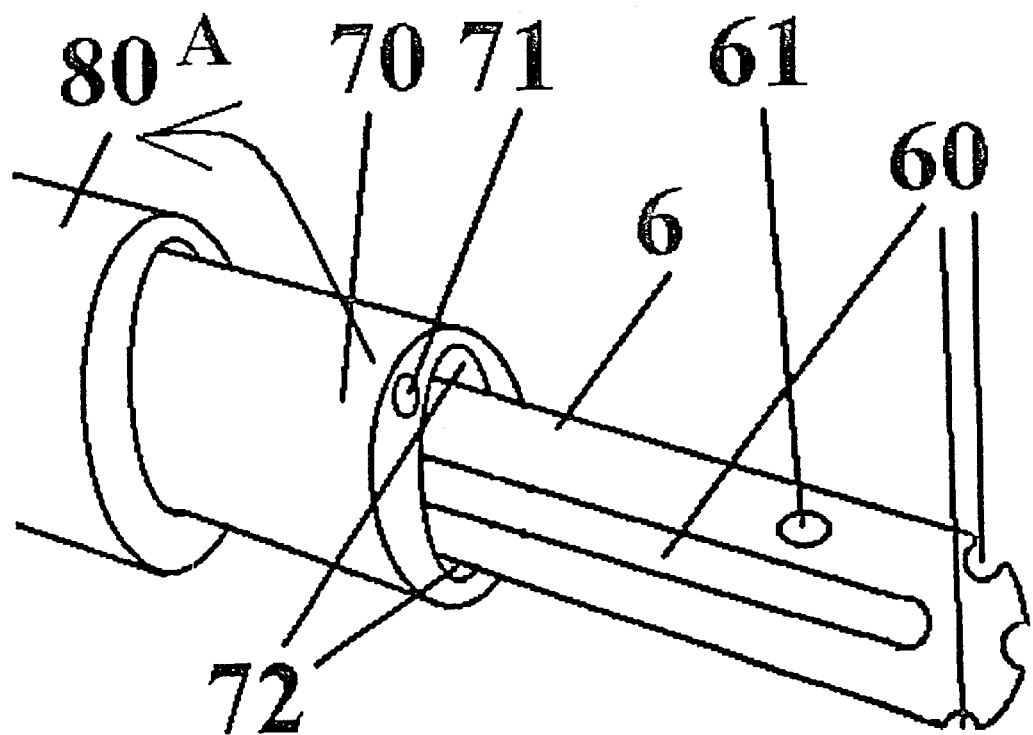
FIG. 8 is a partial perspective view of one embodiment of an ultrasonic treatment apparatus of the present invention.

FIGS. 6 and 8 show features of an ultrasonic treatment apparatus of another embodiment of the present invention. As shown in FIG. 6, the ultrasonic treatment apparatus has an ultrasonic probe 6 with an ultrasonic tip 7. The ultrasonic probe 6 is housed in, for slidable movement within, a flexible articulation sheath 70. The flexible articulation sheath 70 is, in turn, housed in, for slidable movement within, a rigid sheath 80. Rigid sheath 80 is connected to, for movement with, a retracting housing 90. The retracting housing 90 is connected to a retracting trigger 94, which is pivoted on the handle 5. The retracting housing 90 may include an aspiration fitting or luer 13, which is configured for connection with a flexible tube which is in turn connected to a source of reduced pressure. The aspiration fitting or luer 13 is connected to the interior of the flexible articulation sheath 70.

An articulation trigger 91 may be housed on the retracting housing 90. Articulation trigger 91 is connected to an articulation wire 71. A trigger 92 may also be housed on the retracting housing 90. A cover 93 may cover components between the retracting housing 90 and the handle 5. FIG. 8 shows the details of the proximal end of the ultrasonic apparatus of FIG. 6. The ultrasonic probe 6 may include one or more grooves or channels 60 which are used to provide aspiration to the area around the ultrasonic tip 7. One or more irrigation lumens 61 may provide irrigating fluid to the area around the ultrasonic tip 7. The ultrasonic probe 6, which, because of its small cross-sectional profile and the material of which it is constructed, is somewhat flexible so that it may be bent or articulated. The ultrasonic probe 6 fits within, for axial movement, the articulation sheath 70, which is made of a relatively flexible and resilient material. The space 72 between the ultrasonic probe 6 and the articulation sheath 70, together with the grooves or channels 60, form aspiration passages. The articulation sheath 70 may include, at one or more locations around the circumference of the articulation shaft 70, one or more embedded articulation wires 71, with a distal end affixed to the articulation sheath 70. The proximal end of the articulation wire 71 is affixed to the articulation trigger 91. The articulation sheath 70 is housed within, for axial movement, the rigid sheath 80. Rigid sheath 80 is made of a relatively rigid material.

When the rigid sheath 80 is slid back away from the distal end of they articulation sheath 70, and the articulation wire 71 is pulled axially inwardly by the articulation trigger 91, the articulation sheath will bend or articulate in a bending or articulation direction A. As a result, the ultrasonic probe 6 and ultrasonic tip 7 will bend or articulate in articulation direction A. In this way, the ultrasonic can be used to reach locations which are not axially aligned with the lumen or vessel through which the ultrasonic probe 6 is inserted.

In a preferred embodiment of the invention, maximum vibratory motion is not confined to the tip of the probe as in the case of prior art ultrasonic instruments. Rather, the probe of the invention is specially designed to provide a multiplicity of so-called anti-nodes (i.e., points along the probe where maximum vibration occur) at spaced intervals along the axial length of the probe, in addition to the tip of the probe. This construction best suits the method of the invention because removal of tissue will not be confined to those regions of the tissue coming into contact with the tip of the probe. Rather, as the probe is swept through the tissue, preferably in a windshield wiper fashion, the tissue is removed in all areas adjacent to the multiplicity of anti-nodes located along the entire length of the probe. In other preferred embodiments of the invention, the cavitation effect caused by the probe can be directed and/or shaped by a sheath surrounding the probe and having one or more apertures for localizing the cavitation effect. In this way, the apparatus of the invention allows for tissue removal in accordance with the method of the invention to be carried out most efficiently so that actual treatment time is greatly reduced as compared to prior art methods.

Furthermore, the mode of vibration of the ultrasound probe in the apparatus of the invention differs from the axial mode of vibration which is conventional in the prior art. Rather than vibrating exclusively in the axial direction, the probe in the apparatus of the present invention vibrates in a direction transverse to the axial direction. Because of this transverse mode of vibration, the probe of the invention removes tissue not just at those points where the probe makes actual contact with the tissue, but also typically in a region having a radius up to 1.0–1.5 mm around the probe. Hence, the transverse mode of vibration of the probe used in the present apparatus also contributes to the efficiency of the method of the invention by expanding the coverage area around the probe where tissue is removed.

In general, in order to increase the number of anti-nodes occurring along the axial length of the probe, the vibration frequency imparted to the probe should be increased. The frequency, however, is not critical and a generator run at 20 kHz is generally sufficient to provide for an effective number of anti-nodes along the axial length of the probe. In addition, as will be appreciated by those skilled in the art, it is possible to adjust the dimensions of the probe, including diameter, length and location of coupling to the ultrasonic energy source, in order to space the anti-nodes at desired intervals. Applicant's co-pending applications Ser. No. [60/178,901] and Ser. No. 09/625,803 further describe the design parameters for an ultrasonic probe operating in a transverse mode, and is herein incorporated in their entirety by reference.

A significant advantage of the present invention is that it physically destroys and removes adipose or other high water content tissue through the mechanism of non-thermal cavitation, which makes it well suited for use in performing transverse liposuction and plastic surgery procedures. The removal of tissue by cavitation also provides the ability to remove large volumes of tissue with a small diameter probe, without making large holes in the tissue or the surrounding areas. Accordingly, because of the use of cavitation as the mechanism for destroying tissue, together with the use of irrigation and aspiration, the method and apparatus of the present invention can destroy and remove tissue within a range of temperatures of ±7° C. from normal body temperature. Therefore complications attendant with the use of thermal destruction or necrosis of tissue—such as swelling or edema, as well as loss of elasticity are avoided. Furthermore, the use of fluid irrigation can enhance the cavitation effect on surrounding tissue, thus speeding tissue removal.

The cavitation energy is the energy that is expelled from the probe in a stream of bubbles which must contact the tissue to cause ablation. Therefore, blocking the cavitation bubble stream from contacting tissue will spare the tissue from ablation, while directing the cavitation bubble stream to contact the tissue will cause ablation. Referring to FIG. 10, the invention further provides a semi-cylindrical sheath 107 having a semi-rigid wall 120 that surrounds a portion of probe 7 and extends longitudinally along the probe. Sheath 107 has an aperture 108 also extending longitudinally along the probe 7, which aperture provides a window for directing cavitation energy generated by the probe, i.e., the stream of cavitation bubbles, toward the tissue to be removed. Conversely, semi-rigid wall 120 blocks cavitation energy generated by the probe from reaching the tissue on the opposite side of the wall, i.e., the tissue to be spared. The angular extent θ of the sheath may vary depending on the tissue removal requirements, and will generally extend from less than about 180 degrees to more than 270 degrees.

Preferably, sheath 107 is made from thin-walled polymeric material, or another semi-rigid material capable of blocking the cavitation energy generated by the probe. The polymeric, or other material making up the wall of the sheath should be sufficiently thin and rigid to allow ultrasonic energy to pass through the wall without significant absorption. The sheath material should preferably be lubricious to aid in sliding the probe and sheath along the tissue.

Referring to FIG. 11, an outer cylindrical sheath 109 can be used to adjust the length l of the effective aperture 108(a) exposed along semi-cylindrical sheath 107 by covering the aperture along a portion of the length of semi-cylindrical sheath 107 and leaving a portion of the aperture exposed. The outer cylindrical sheath 109 sheath can be moved along the axis of the semi-cylindrical sheath 107 to adjust the effective aperture length l and thereby adjust the amount of tissue to be removed. The sheath can also be provided with a rounded or shaped tip that can be smoothly introduced into tissue between other tissue layers, such as the adipose tissue between skin and muscle, so that introduction and advancement of the probe and sheath causes minimal trauma to the surrounding tissues. The profile of the probe and sheath can be selected so that introduction of the probe and sheath will dissect or transect the tissue in a minimally traumatic manner. The sheath can also be used to introduce irrigation fluids into the operative site and provide a mechanism for aspiration of emulsified tissue and fluids.

The geometry and operation of the probe allows for a sweeping ablation and removal of tissue along the length of the probe (or its effective aperture) using either a linear or an arctuate movement to provide more even removal, and therefore more even remodeling, of the target tissue than any of the methods known in the art. For example, liposuction, a medical procedure for the aspiration and evacuation of fat from under the skin that is conventionally performed by applying a negative pressure to a cannula, or a plain suction tube, which is moved under the skin surface through an incision. The removal of adipose tissue using traditional liposuction methods often results in the formation of dimples, pockets and ridges caused by the localized removal of tissue by punching and pushing with a force provided only from the tip of the cannulas. The present invention provides a method of removal of adipose tissue without the need for punching and pushing because when the probe of the present invention is inserted into the tissue, transverse energy in a wet environment emulsifies the tissue forming a lengthwise cavity around the probe. The probe can then be moved in a sweeping fashion to remove a plane layer of the tissue without causing punching or pushing trauma to the tissue. Because the probe can be moved about a pivot point in a windshield wiper type of movement, the probe may be inserted into the issue through a very small incision, yet sweep through and remove a large angular sector of tissue along the length of the inserted probe. The method of the present invention therefore provides better sculpting of the adipose tissue and a more even end-result as the force is provided along the long axis of the probe and the movement of the probe is sweeping rather than pushing or punching which can cause dimples, pockets and ridges. Irrigation can be used to enhance the cavitation effect on the tissue, and emulsified tissue can be removed by aspiration. Tumescent procedures that introduce large volumes of fluid and anesthetics into the operative site can also enhance the operation of the probe.

Referring to FIGS. 12(a) and 12(b), the invention further provides a cylindrical sheath 121 shown with one or more apertures 111 along its length. The apertures can be round, square, or oval, in shape and provide a focused area of treatment where the intensity of the cavitation energy can be enhanced by the function of the sheath. That is, cavitation energy will only pass though the apertures to ablate adjacent tissue, and be blocked by the remainder of the sheath to spare other tissue. The apertures 111 can be spaced and shaped such that they are capable of defining the shape and space associated with the stream of cavitation bubbles.

Figure 13:
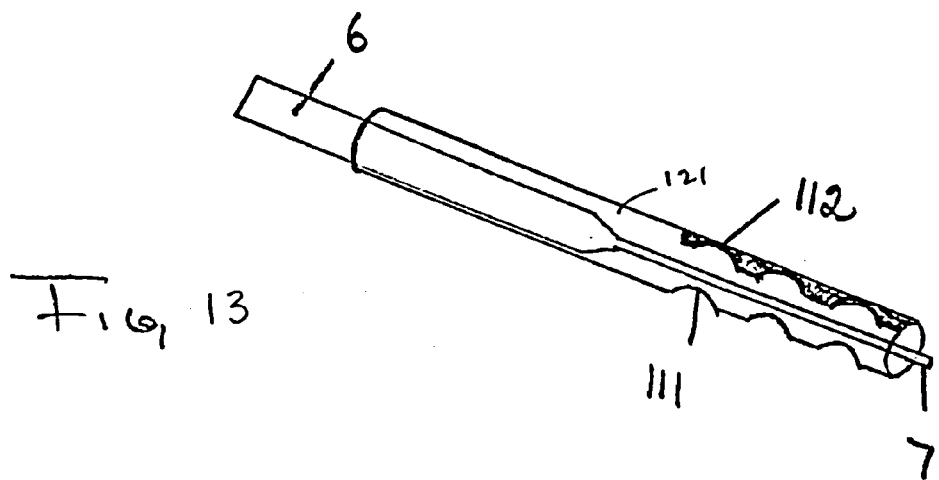
FIG. 13 shows a cylindrical sheath that has acoustic lenses on the inner surface of the sheath allowing focusing and intensifying of the cavitation energy emitted through the apertures.

Referring to FIG. 13, the cavitation energy emitted from the probe can be further focused using acoustic lenses 112 fashioned inside sheath 121 opposite the apertures 111. Lenses 112 reflect and focus cavitation energy through apertures 111 to enhance the intensity of the cavitation energy emitted through the apertures so as to focus and intensify the energy directed towards to the treatment area.

Figure 14:
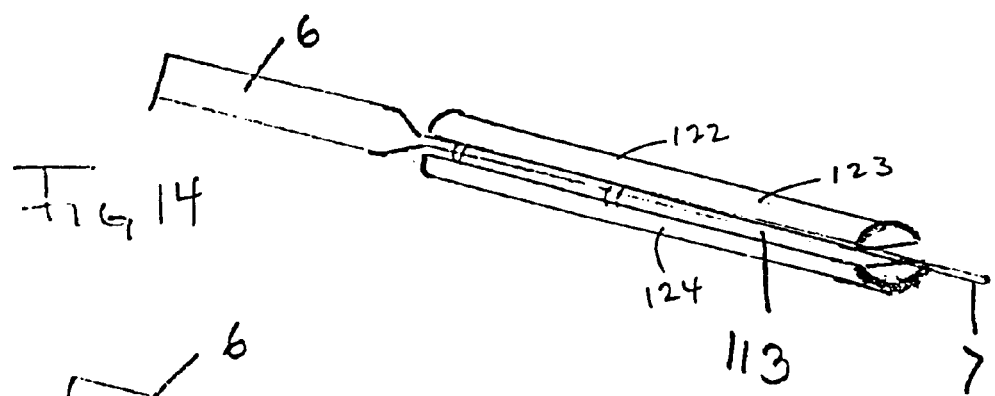
FIG. 14 shows a sandwich-like aperture that can be made to direct the cavitation energy emitted by the probe.

Referring to FIG. 14, another embodiment of a sheath 122 is formed from two parallel semi-cylindrical sections 123 and 124 extending along the length of probe 7 that are spaced apart in a sandwich-like fashion to form apertures 113 along opposite sides of the probe. This configuration will emit cavitation energy substantially along a plane coincident with the long axis of the probe allowing formation of a flat, fan-like pattern.

Figure 15:
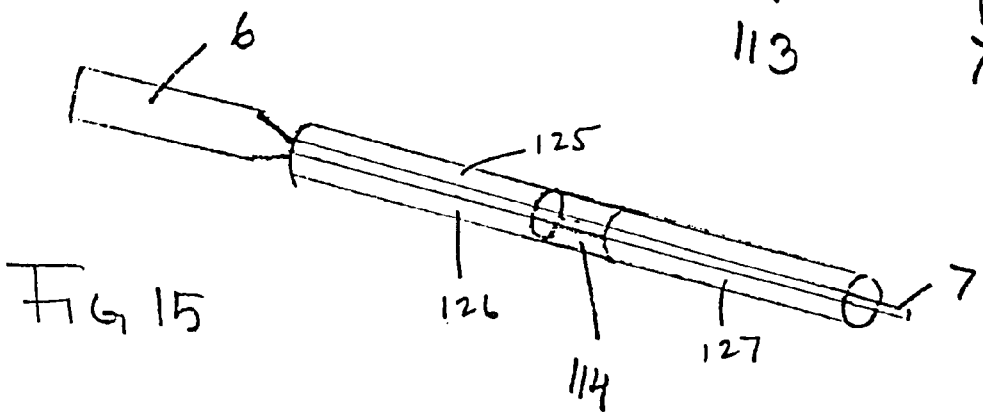
FIG. 15 shows an annular aperture that can be made to direct the cavitation energy emitted by the probe in a radial pattern.

Referring to FIG. 15, another embodiment of a sheath 125 is formed from two cylindrical section 126 and 127 extending along the length of probe 7 and separated by an annular aperture 114. This configuration will emit cavitation energy substantially radially along a plane perpendicular to the long axis of the probe allowing formation of a disk pattern.

The sheaths describe may be used to cover the probe to further refine remodeling performed in delicate areas, such as is facial liposuction or tissue remodeling of the eye lids. The apertures can further be covered with an outer cylindrical sheath described above. All the above described sheaths can be introduced and controlled with known techniques such as attaching the sheaths to, e.g., a guide-wire. Use of a larger diameter sheath can protect tissue from accidental penetration by an ultrasonic probe that may be stiffer than the surrounding tissue.

The sheath can be of fixed size and the sizes may vary depending on the size of the target tissue to be removed and the length of the probe. The size of the apertures of the sheath can also vary depending on the amount of cavitation energy that is desired to be directed to the target tissue.

The present invention can similarly be used to remove benign cysts or growth from the breast tissue with minimally invasive techniques. The probe with or without the sheath is introduced into the tissue and the energy is provided along the extent of the growth to be removed.

The probe of the present invention can be of variable diameter and length so that it can be used to remove tissue smoothly in areas such as eye lids and areas requiring precision such as around the face.

The probe of the present invention is particularly useful in a treatment technique in which the treated area may be imaged by ultrasound imaging, in particular color ultrasound. The vibrating action of the probe echogenically produces a pronounced and bright image on the ultrasound, and therefore is readily viewable and discernable as the probe (as opposed to surrounding tissue) by the surgeon or physician, greatly increasing the ease of use and effectiveness of treatment. For example, the ultrasound transducer probe can be used to visualize the cyst or other benign growth during the removal of cysts or other benign growth in the breast where the ultrasound transducer may be located on the surface of the skin. The method of the present invention can also be used in combination with magnetic resonance imaging without interfering with the quality of the image as the ultrasonic waves cause no magnetic fields and the titanium alloy material of the ultrasonic probe in non-magnetic.

While the invention has been particularly shown and described with reference to the preferred embodiments thereof, it will be understood by those skilled in the art that various changes in form and details may be made therein without departing from the spirit and scope of the invention as defined by the appended claims.

What is claimed is:

1. A method of destructing, reducing or removing tissue with an ultrasonic device comprising a transducer capable of providing an ultrasonic excitation signal to a probe, said probe having a proximal end, a distal end, and a longitudinal axis therebetween, coupled to said transducer, said probe capable of transverse vibrations along its longitudinal axis, comprising the steps of:
   i) placing the probe in contact with the tissue;
   ii) providing an ultrasonic electrical excitation signal to said ultrasonic device and providing a means for transferring the signal to a flexible probe tip to cause transverse vibration of said probe and the generation of a plurality of transverse vibration anti-nodes of cavitation energy along the longitudinal axis of said probe; and
   iii) fragmenting or emulsifying the tissue with the cavitation energy emitted by said probe.

2. The method of claim 1 further comprising placing the probe at least partially within a sheath assembly consisting of at least one sheath.

3. The method of claim 2 further comprising positioning said probe and sheath assembly having at least one fenestration such that said fenestration is in proximity with the tissue.

4. The method of claim 2 further comprising removing fragments of the tissue through an aspiration means of the sheath assembly.

5. The method of claim 2 further comprising supplying an irrigating fluid to the site of tissue removal through a fluid conduit of the sheath assembly to provide an irrigation means.

6. The method of claim 2 further comprising positioning said probe proximal to said tissue through an imaging means of the sheath assembly.

7. The method of claim 2 further comprising manipulating the probe and the sheath assembly through an articulation means of the sheath assembly.

8. The method of claim 1 wherein the tissue is adipose tissue.

9. The method of claim 1 wherein the tissue is a benign cyst or cellular growth in a human breast.

10. The method of claim 1 wherein the tissue is part of the eyelid or ocular sac.

11. An ultrasonic medical device comprising:
   a probe having a distal end, a proximal end and an axial length therebetween; and
   a diameter of the probe that is tapered from the proximal end of the probe to the distal end of the probe,
   wherein the probe supports a transverse ultrasonic vibration along at least a portion of the axial length of the probe, producing a plurality of transverse vibration anti-nodes along at least a portion of the axial length of the probe.

12. The ultrasonic medical device of claim 11 wherein the probe has a small cross sectional profile that allows insertion of the ultrasonic medical device into a vasculature.

13. The ultrasonic medical device of claim 11 wherein the probe is axially movably mounted within an aspiration sheath, the aspiration sheath having a proximal end, a distal end, and an axial length therebetween.

14. The ultrasonic medical device of claim 11 further comprising a probe tip capable of moving axially inward and outward relative to the distal end of an aspiration sheath.

15. The ultrasonic medical device of claim 14 wherein the probe tip is a ball shaped projection from the distal end of the probe.

16. The ultrasonic medical device of claim 11 wherein the probe includes a groove for aspiration of a material from a treatment site.

17. The ultrasonic medical device of claim 11 wherein the transverse ultrasonic vibration of the probe provides a plurality of anti-nodes along at least a portion of the axial length of the probe.

18. The ultrasonic medical device of claim 11 wherein the probe comprises a titanium alloy.

19. The ultrasonic medical device of claim 11 wherein a flexibility of the probe allows the probe to be articulated.

20. A medical device comprising:
   a flexible probe having a distal end, a proximal end and an axial length therebetween; and
   a probe tip extending from the distal end of the probe,
   wherein the probe is capable of flexing to support a transverse ultrasonic vibration along at least a portion of the axial length of the probe, producing a plurality of transverse vibration anti-nodes along at least a portion of the axial length of the probe.

21. The medical device of claim 20 wherein the flexible probe has a small cross sectional profile that allows insertion of the flexible probe into a treatment site.

22. The medical device of claim 20 wherein the flexible probe is axially movably mounted within an aspiration sheath, the aspiration sheath having a proximal end, a distal end, and an axial length therebetween.

23. The medical device of claim 20 wherein the probe tip is capable of moving axially inward and outward relative to the distal end of an aspiration sheath.

24. The medical device of claim 20 wherein the probe tip is a ball shaped projection from the distal end of the flexible probe.

25. The medical device of claim 20 wherein the flexible probe includes a groove for aspiration of a material from a treatment site.

26. The medical device of claim 20 wherein the transverse ultrasonic vibration of the flexible probe provides a plurality of anti-nodes along at least a portion of the axial length of the flexible probe.

27. The medical device of claim 20 wherein the flexible probe comprises a titanium alloy.

28. The medical device of claim 20 wherein the flexibility of the probe allows the probe to be articulated.

* * * * *